(12) United States Patent
Krasnow et al.

(10) Patent No.: US 9,861,756 B1
(45) Date of Patent: Jan. 9, 2018

(54) APPARATUS AND METHODS FOR TRACKING ADMINISTERING OF MEDICATION BY SYRINGE

(71) Applicant: Verily Life Sciences LLC, Mountain View, CA (US)

(72) Inventors: Benjamin David Krasnow, Redwood City, CA (US); Peter Howard Smith, Pacifica, CA (US); Travis Deyle, San Jose, CA (US); Russell Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/133,396

(22) Filed: Apr. 20, 2016

Related U.S. Application Data

(60) Provisional application No. 62/305,067, filed on Mar. 8, 2016.

(51) Int. Cl.
*A61M 31/00* (2006.01)
*A61M 5/315* (2006.01)

(52) U.S. Cl.
CPC ..... *A61M 5/31568* (2013.01); *A61M 2205/18* (2013.01); *A61M 2205/332* (2013.01);
(Continued)

(58) Field of Classification Search
CPC .......... A61M 5/31525; A61M 5/31533; A61M 5/31565; A61M 5/16831; A61M 5/315; A61M 2205/60; A61M 2205/33; A61M 2205/35; A61M 2205/3515; A61M 2205/3523; A61M 2205/3569; A61M 5/3375; A61M 2205/3375; A61M 2205/3368; A61M 2205/332; A61M 2205/18; A61M 2205/3592;
(Continued)

(56) References Cited

U.S. PATENT DOCUMENTS 4,358,839 A * 11/1982 Wittke ................ H03K 21/40
331/158
5,311,871 A 5/1994 Yock
(Continued)

OTHER PUBLICATIONS

PCT/US2017/017821—International Search Report and Written Opinion dated Jun. 8, 2017, 16 pages.

*Primary Examiner* — Kevin C Sirmons
*Assistant Examiner* — Tiffany Legette-Thompson
(74) *Attorney, Agent, or Firm* — Christensen O'Connor Johnson Kindness PLLC

(57) ABSTRACT

An apparatus and methods for tracking administering of medication by syringes is provided. The apparatus may include a plunger head for a syringe. The plunger head may include a transducer that sends and receives ultrasonic signals. The plunger may also include an antenna and a microcontroller that interfaces with the transducer and the antenna. The plunger may also include a power source that powers the microcontroller and the transducer. The transducer, the antenna, the microcontroller, and the power source may be at least partially encapsulated in an elastomer housing that fits within a barrel of the syringe. The microcontroller may be programmed with instructions to calculate data representative of the quantity of medication dispensed from the barrel and transmit the data to a remote device via the antenna.

12 Claims, 3 Drawing Sheets

(52) U.S. Cl.
CPC ............... *A61M 2205/3368* (2013.01); *A61M 2205/3375* (2013.01)

(58) Field of Classification Search
CPC ..... A61M 5/31568; A61M 2205/31545; G01F 13/00; G01F 13/006
USPC .......................... 604/67, 207, 189, 506, 246
See application file for complete search history.

(56) References Cited

U.S. PATENT DOCUMENTS

| | | |
|---|---|---|
| 5,678,189 A | 10/1997 | Barnes |
| 5,728,074 A | 3/1998 | Castellano et al. |
| 5,826,066 A * | 10/1998 | Jardine .................... G06F 1/14 713/400 |
| 6,585,698 B1 | 7/2003 | Packman et al. |
| 7,927,281 B2 | 4/2011 | Wheeler |
| 8,226,599 B2 | 7/2012 | Engle |
| 8,556,866 B2 | 10/2013 | Krulevitch et al. |
| 8,560,271 B2 | 10/2013 | Koehler et al. |
| 8,817,258 B2 | 8/2014 | Whalley et al. |
| 9,008,764 B2 | 4/2015 | Larsen |
| 9,101,723 B2 | 8/2015 | Larsen |
| 9,250,111 B2 | 2/2016 | Whalley et al. |
| 9,255,830 B2 | 2/2016 | Whalley et al. |
| 2005/0209601 A1* | 9/2005 | Bowman ............. A61B 17/8805 606/90 |
| 2008/0188813 A1 | 8/2008 | Miller et al. |
| 2008/0243088 A1 | 10/2008 | Evans |
| 2009/0043253 A1 | 2/2009 | Podaima |
| 2009/0069742 A1 | 3/2009 | Larsen |
| 2011/0009824 A1* | 1/2011 | Yodfat ............... A61M 5/14248 604/151 |
| 2012/0101451 A1* | 4/2012 | Boit ..................... A61M 5/1424 604/224 |
| 2012/0302849 A1* | 11/2012 | Grant ................. A61M 5/14244 600/365 |
| 2013/0116666 A1* | 5/2013 | Shih ...................... A61M 5/162 604/891.1 |
| 2013/0310756 A1* | 11/2013 | Whalley ................. A61M 5/31 604/189 |
| 2014/0249410 A1* | 9/2014 | Uber, III ........... A61M 5/31573 600/432 |
| 2014/0379874 A1 | 12/2014 | Starr et al. |
| 2015/0112316 A1 | 4/2015 | Cudak et al. |
| 2015/0174342 A1 | 6/2015 | Mitrosky et al. |
| 2015/0209510 A1 | 7/2015 | Burkholz et al. |
| 2016/0030683 A1 | 2/2016 | Taylor et al. |
| 2016/0074587 A1 | 3/2016 | Searle et al. |

* cited by examiner

APPARATUS AND METHODS FOR TRACKING ADMINISTERING OF MEDICATION BY SYRINGE

RELATED APPLICATIONS

This application claims the benefit of U.S. Provisional Application No. 62/305,067, filed Mar. 8, 2016, which is incorporated by reference in its entirety.

BACKGROUND

Technical Field

The present disclosure relates generally to the field of tracking administering of medication, and more particularly, apparatus and methods for tracking administering of medication by syringes.

Background Description

Measuring the quantity and recording the timing of a drug's administration is an integral part of many disease treatments. For many treatments, to achieve the best therapeutic effect, specific quantities of a drug may need to be injected specific times of day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range. Currently, there are a limited number of methods or devices for automatically tracking the drug administration without requiring the user to manually measure and record the volume, date, and time. A variety of glucose injection syringes/pens have been developed, but there is much room for significant advancement in the technology in order to reduce the size, lower the cost, and enhanced the functionality thus making them a more viable long term solution. For example, current insulin pens are often disposable, but do not include dosage tracking. A smaller portion of the market is composed of reusable pens which are more expensive, and still don't include good dosage tracking capabilities.

SUMMARY

The present disclosure is directed to systems and methods of drug administration using a syringe with a smart plunger head.

In one aspect, the present disclosure is directed to a plunger head for a syringe. The plunger head may include a transducer that sends and receives ultrasonic signals. The plunger may also include an antenna and a microcontroller that interfaces with the transducer and the antenna. The plunger may also include a power source that powers the microcontroller and the transducer. The transducer, the antenna, the microcontroller, and the power source may be at least partially encapsulated in an elastomer housing that fits within a barrel of the syringe. The microcontroller may be programmed with instructions to calculate data representative of the quantity of medication dispensed from the barrel and transmit the data to a remote device via the antenna.

In another aspect, the present disclosure is directed to a system for tracking administering of a medication dispensed by a syringe. The system may include a plunger head that fits within a barrel of the syringe. The plunger head may include a transducer that sends and receives ultrasonic signals and a first antenna. The plunger head may also include a first microcontroller that interfaces with the transducer and the antenna. The system may also include a cuff that is attachable to the barrel of the syringe. The cuff may include a second microcontroller, a second antenna that receives information from the plunger head via the first antenna, and a power source. The first microcontroller may be programmed with instructions to measure the time it takes for the ultrasonic signals to travel through the medication in the syringe to an end of the barrel and return to the transducer, the second microcontroller may be programmed with instructions to calculate data representative of the quantity of medication dispensed from the barrel based on a change in the time measured.

In another aspect, the present disclosure is directed to a method of tracking administering of a medication delivered by syringe. The method may include depressing a plunger of the syringe. The method may also include sending and receiving ultrasonic signals from a plunger head installed within a barrel of the syringe. The method may further include measuring the time it takes for the signals to travel through the medication to an end of the barrel and return to the transducer. The method may also include calculating the distance the plunger head travels based on a change in the time and calculating a quantity of the medication dispensed based on the distance the plunger head travels. The method may further include selectively transmitting wirelessly the quantity of the medication dispensed to a remote device.

In another aspect, the present disclosure is directed to a plunger head for a medication injection device. The plunger head may include a transducer that sends and receives ultrasonic signals and an antenna. The plunger head may also include a microcontroller that interfaces with the transducer and the antenna, and a power source that powers the microcontroller and the transducer. The transducer, the antenna, the microcontroller, and the power source may be at least partially encapsulated in an elastomer housing that fits within a barrel of the medication injection device. The microcontroller may be programmed with instructions to calculate data representative of the quantity of medication dispensed from the barrel and transmit the data to a remote device via the antenna.

DETAILED DESCRIPTION

Reference will now be made in detail to embodiments of the present disclosure, examples of which are illustrated in the accompanying drawings. Where possible, the same reference numbers will be used throughout the drawings to refer to the same or like parts.

Figure 1:
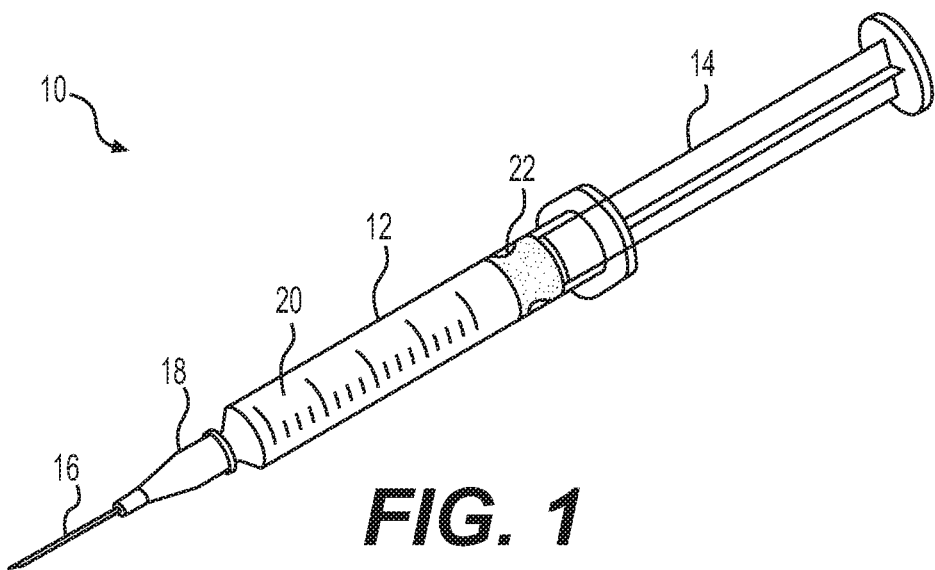
FIG. 1 is a perspective view of a syringe, which includes a plunger head according to an exemplary embodiment.

FIG. 1 shows a perspective view of a syringe 10 designed for ejecting a fluid. Syringe 10 may include a barrel 12, a plunger 14, a needle 16, and a hub 18 connecting needle 16 to barrel 12. Barrel 12 may be configured to contain a fluid, for example, a medication 20 and syringe 10 may be configured to dispense medication 20 from needle 16 when plunger 14 is depressed. A standard syringes usually contains a plunger head at the end of the plunger that seals the top of the barrel and forces the fluid out the needle when the plunger is depressed. The plunger head for a standard syringe is usually just a piece of molded plastic.

For Syringe 10 shown in FIG. 1, the standard plunger head has been replaced with a smart or intelligent plunger head 22 that is configured to measure and register the quantity of medication 20 administered and the date and time of administration. Plunger head 22 may be installed in a standard syringe by withdrawing plunger 14 and removing the standard plunger head and installing smart plunger head 22. In some embodiments, syringe 10 may be manufactured and supplied with a smart plunger head 22 preinstalled. Smart plunger head 22 may be referred herein as either smart plunger head 22 or plunger head 22.

Plunger head 22 may be sized to correspond with the size of barrel 12. For example, plunger head 22 may be formed to fit any size syringe. For example, plunger head 22 may be sized to fit a 1 ml, 2 ml, 3 ml, 5 ml, 10 ml, 20 ml, 30 ml, or 50 ml syringe.

Figure 2:
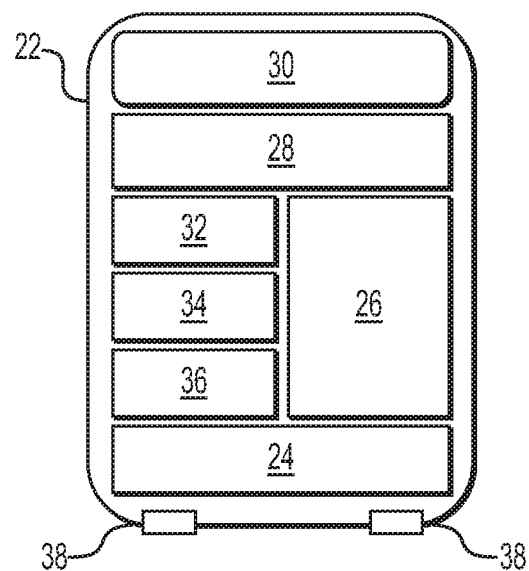
FIG. 2 is a schematic of the plunger head of FIG. 1.

FIG. 2 shows a schematic of plunger head 22, according to an exemplary embodiment. Plunger head 22 may include a transducer 24, a microcontroller 26, a power source 28, and an antenna (e.g., for near field communication (NFC) or a transceiver 30 (e.g., for BLUETOOTH low energy (BLE) communication). In some embodiments, the components of plunger head 22 may be at least partially encapsulated in an elastomer (e.g., rubber, ethylene propylene (EPM), Nitrile (NBR), ethylene propylene diene (EPDM), polybutadiene, and polisoprene). Transducer 24 may be configured to send and receive ultrasonic signals. Microcontroller 26 may be programmed with instructions to control the overall operation of the plunger head. Transceiver 30 may be configured to wirelessly communication with a remote device (e.g., a smart phone, a glucose monitor, an insulin pump, and a computer) using one or more wireless communication methods. The one or more wireless communication methods may include, for example, radio data transmission, Bluetooth, (BLE), (NFC), infrared data transmission, electromagnetic induction transmission, and/or other suitable electromagnetic, acoustic, or optical transmission methods. Power source 28 may be configured to power transducer 24, microcontroller 26, and transceiver 30.

Figure 3:
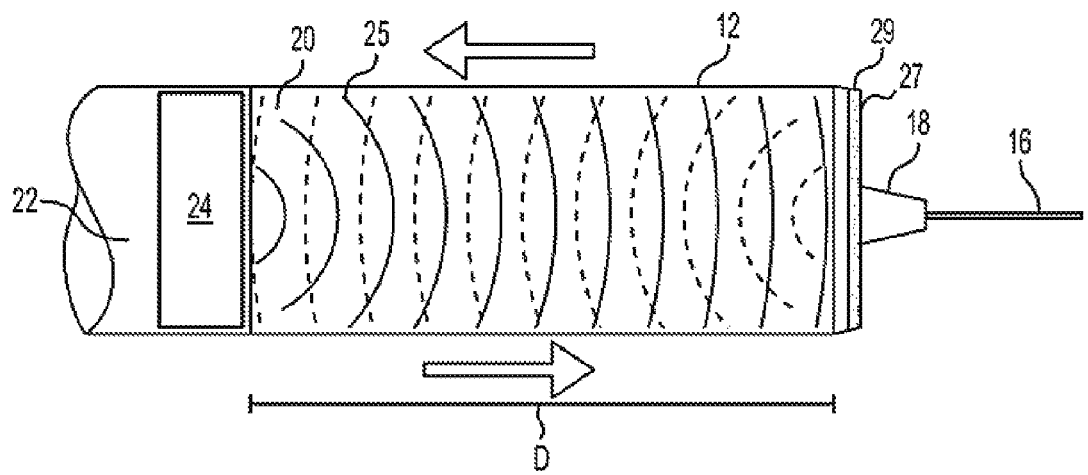
FIG. 3 is a schematic illustrating the behavior of ultrasonic signals transmitted by the plunger head of FIG. 2.

Transducer 24 may be an actuator, piezoelectric element, or speaker-like voice coil configured to generate and send a pressure wave or ultrasonic signal. Transducer 24 may be sized to be slightly smaller than the inner diameter of barrel 12. As shown in FIG. 3, transducer 24 may be configured to generate ultrasonic signals 25 (e.g., radiated sound energy waves) and send the ultrasonic signals 25 down barrel 12 toward hub 18 and needle 16. The ultrasonic signals can travel through medication 20 along the length of barrel 12 and bounce or reflect off an end 27 of barrel 12 and travel back through medication 20 to plunger head 22. The reflected ultrasonic signals can be received and detected by transducer 24. The speed of sound in medication 20 may be a known value and thus a distance D can be calculated very accurately based on the time it takes for a ultrasonic signal to travel down and back from transducer 24. As plunger head 22 is moved down barrel 12 distance D will change and by knowing the diameter of barrel 12 then the volume of medication 20 dispensed may be calculated based on the change in distance D.

In some embodiments a portion of the transducer 24 may make direct physical contact with medication 20 (e.g., for the best impedance matching). For embodiments where transducer 24 makes direct contact with medication 20, transducer 24 may be coated to prevent chemical interactions or to improve mechanical impedance matching between the transducer and medication 20. In some embodiments, transducer 24 may be molded directly into the material (e.g., elastomer) of the plunger head 22. It is contemplated that there are a variety of configures for maximizing the transfer of ultrasonic signals 25 from transducer 24 to medication 20 and from medication 20 to transducer 24.

In some embodiments, transducer 24 may be configured to vibrate in order to numb the needle injection site so that the pain is reduced.

As shown in FIG. 3, in some embodiments, a porous membrane 29 may be placed within barrel 12 at end 27. Porous membrane 29 may be designed to allow medication 20 to pass through while providing a surface with good reflective properties for the ultrasonic signals 25 to reflect from. Utilizing porous membrane 29 may improve the accuracy of the reflective wave detection and thereby the distance and volume calculations. It is contemplated that other materials may be used besides a porous membrane. It is also contemplated that the geometry of barrel 12 at end 27 may dictate whether a porous membrane is needed. For example, in some embodiments the geometry of end 27 may be designed to produce the desired reflective properties avoiding the need to porous membrane 29.

Microcontroller 26 may include one or more processors, including for example, a central processing unit (CPU). The processors may include any suitable type of commercially available processor or may be a custom design. Microcontroller 26 may include additional components, for example, non-volatile memory (e.g., a flash memory), volatile memory (e.g., a random access memory (RAM)), and other like components, configured to store information).

Microcontroller 26 may be programmed with instructions to control the operation of transducer 24. Microcontroller 26 may be programmed with instructions to calculate data representative of the quantity of medication 20 dispensed. For example, in some embodiments, microcontroller 26 may be programmed to detect and record the reflection times of the ultrasonic signals 25. Based on the reflection times, microcontroller 26 may track and produce a time profile of the distance between transducer 24 (i.e., plunger head 22) and end 27. Based on the time profile of the distance, microcontroller 26 may be able to identify a first distance $D_1$ or starting position (e.g., before medication 20 is dispensed), which may correspond with barrel 12 being filed and a second distance $D_2$ or ending position (e.g., after medication 20 is dispensed), which may correspond with barrel 12 being empty. Microcontroller 26 may then calculate the change in distance between $D_1$ and $D_2$ and based off of the change in distance may calculate the volume (i.e., amount or quantity) of medication 20 dispensed.

In some embodiments, medication 20 may include an active medication ingredient and a buffer solution. The concentration of the active medication ingredient may be known or programmed into microcontroller 26 enabling the specific volume of the active medication ingredient to be calculated. In some embodiments, for example, the concentration of the active medication ingredient may be stored in the non-volatile memory of microcontroller 26. In some embodiments, additional information regarding the medication 20 may also be stored, for example, ultrasonic velocity vs. temperature data.

In some embodiments, in addition to calculating the volume of medication 20 as it is dispensed, plunger head 22 may first calculate the volume of medication 20 while it was initially loaded into syringe 10. For example, in some embodiments, plunger head 22 may send and receive ultrasonic signals while medication 20 is being drawn into barrel 12. Calculating both the volume of medication 20 as it is loaded and dispensed can act as a verification or double check.

Transducer 24 and/or microcontroller 26 may be programmed to perform various forms of signal conditioning in order to detect the time of the reflected ultrasonic signals 25. The signal conditioning may include, for example, amplification, filters, and envelope detection. Transducer 24 and/or microcontroller 26 may use the signal conditioning to determine for example, time to first rising edge or time to maximum reflective value in order to determine the reflection time.

Plunger head 22 may transmit the amount of medication 20 dispensed along with the time and date it was dispensed to a remote device (e.g., a smart phone, a glucose monitor, an insulin pump, and a computer) via one or more of the wireless communication methods. Plunger head 22 may have a unique identifier so the remote device may be able to identify and process the information received properly. Plunger head 22 may transmit this information to the remote device immediately or shortly after the medication is administered or plunger head 22 may store the information until the remote device is within range. The information may be stored, for example, in memory of microcontroller 26. In some embodiments, plunger head 22 may wait to initiate transmitting of the information to the remote device until initiated by the remote device. For example, a user may initiate information retrieval on the remote device. In some embodiments, the remote device may transmit the information to a caregiver (e.g., a doctor) or upload the information to the cloud so it may be saved to the patient's medical history and may be accessed by the caregiver. The ability of a caregiver or a patient to access and review the dose history may improve treatment. For example, the ability of a caregiver to review a diabetic insulin injection history and continuous glucose measurement data may enable the caregiver to adjust the prescribe treatment to improve the therapeutic effect, for example, by better stabilizing the patients glucose levels.

In some embodiments, microcontroller 26 may be configured to simply detect the reflection time of the ultrasonic signals 25 and transmit that to the remote device and the remote device may perform all the calculations. For example, in some embodiments, plunger head 22 may be a passive device (e.g., battery free) and the remote device may utilize near field communication (NFC) to control microcontroller 26 and transducer 24. For embodiments where plunger head 22 is a passive device, plunger head 22 may rely on the remote device to keep track of the date and time. By simplifying the functionality of plunger head 22 the cost of manufacturing may be reduced.

In some embodiments, plunger head 22 may also include a crystal oscillator 32 configured to keep accurate time so that the date and time of each injection may be accurately recorded and stored in memory of microcontroller 26. Crystal oscillator may be, for example, a 32 KHZ crystal oscillator. In some embodiments, microcontroller 26 may include an internal RC oscillator, which may be calibrated using crystal oscillator 32. The internal RC oscillator may be, for example, a 10 MHZ RC oscillator. Internal RC oscillator may provide sufficient time accuracy to measure the position (e.g., distance D) of plunger head 22 to within, for example, about 150 microns. In some embodiments, transducer 24 may be used as an oscillator or as a calibrator for the internal RC oscillator. In some embodiments, the frequency of the RC oscillator may be up-converted on microcontroller 26 to a higher frequency. For example, the RC oscillator may be used to drive a higher-frequency phase-locked loop.

Power source 28 may be any suitable power source. For example, power source 28 may be a battery, a capacitor, or the like. In some embodiments, power source 28 may be rechargeable via wireless energy transmission, for example, inductive coupling, resonant inductive coupling, radio frequency (RF) link, or the like. In some embodiments, power source 28 may be a non-rechargeable battery that is configured to last the operational life of plunger head 22, for which the operational life may be about 1 year, about 2 years, about 3 years, or more. For example, in some embodiments, power source 28 may be a watch battery. In some embodiments, where plunger head 22 is a passive device as described herein, power source 28 may be eliminated.

Antenna or transceiver 30 may be used to communicate with a variety of remote devices (e.g., smart phones, glucose monitors, insulin pumps, computers, etc.). Plunger head 22 may transmit the information via any suitable wireless communication method. For example, in some embodiments, plunger head 22 may utilize radio data transmission, BLUETOOTH or (BLE), (NFC), infrared data transmission or other suitable method. In some embodiments, information may also be wirelessly transmitted from a remote device to plunger head 22 via antenna 30. For example, the date and time may be set by writing to microcontroller 26 via the wireless communication.

In some embodiments, plunger head 22 may also include a force sensor 34. Force sensor 34 may be configured to detect when a force is applied to plunger head 22 via plunger 14, which for example may indicate that dispensing of medication is going to be initiated. Force sensor 34 may be, for example, a simple spring-loaded switch that is molded into the plunger head 22.

In some embodiments, plunger head 22 may be configured to only initiate sending and receiving of the ultrasonic signals 25 after force sensor 34 has detected a force, which indicates dispensing is going to be initiated. Prior to detecting the force, plunger head 22 may be in a low-power sleep state that is designed to conserve power (e.g., battery life.) while still keeping accurate track of the date and time. In some embodiments, force sensor 34 may be configured to detect a force when the medication is being loaded or drawn into syringe 10 and cause plunger head 22 to "wake up."

In some embodiments, transducer 24 may be configured to function as a force sensor thereby eliminating the need for a separate force sensor 34. For example, transducer 24 may have a piezoelectric element that may detect the dynamic changes in pressure when a user depresses the plunger 14.

In some embodiments, plunger head 22 may also include a temperature sensor 36. Temperature sensor 36 may be configured to measure the temperature of medication 20. Microcontroller 26 may be configured to use the temperature of medication 20 to compensate for variations in the temperature that would affect the speed of sound within the medication, thus improving the accuracy of the distance and volume calculations.

In some embodiments, microcontroller 26 may also use temperature sensor 36 to monitor the temperature of medication 20 to ensure that the temperature of medication 20 stays within an acceptable range. The efficacy of some medications is affected by temperature. For example, insulin is sensitive to hot and cold temperature. Plunger head 22 thus may use temperature sensor 36 to monitor the temperature of medication 20 and if the temperature of the medication 20 goes beyond the acceptable range then plunger head 22 may be configured to send an alert. The type of alert may vary. In some embodiments, plunger head 22 may include a display (not shown in FIG. 2) and the alert may be a flashing light or a visual indicator. In some embodiments, plunger head 22 may include a speaker and the alert may be auditory, for example, a beeping sound. In some embodiments, the alert may be transmitted to a remote device and the remote device may display a visual alert and/or play an auditory alert.

In some embodiments, plunger head 22 may also be configured to detect air bubbles in medication 20. Air bubbles if injected can be deadly so detection of air bubbles is advantageous. In order to detect air bubbles, transducer 24 of plunger head 22 may be configured to detect small ultrasonic echoes created by the reflection of the ultrasonic waves off the air bubbles in addition to the main echo caused by the end of barrel 12. Plunger head 22 may be configured to transmit an alert if air bubbles are detected. The alert may be communicated in the same ways as the temperature alert described above.

In some embodiments, plunger head 22 may also be configured to differentiate, verify, and/or identify medication 20 contained in syringe 10. For example, when barrel 12 is loaded with medication 20, plunger 14 and plunger head 22 may be pulled all the way back to its stopping point and the distance from plunger head 22 to end 27 of barrel 12 may be known enabling microcontroller 26 to solve for the speed of sound of the fluid, which depends on temperature and density. The temperature may be measured by temperature sensor 36 so the density may be determined and based on the density the amount of solids dissolved in the fluid may also be determined. In addition, the viscosity of the medication 20 may be measured based on the amplitude of the reflected ultrasonic signals 25 because more viscous fluids dissipate more energy. In some embodiments, plunger head 22 may also include electrodes 38 connected to microcontroller 26 configured to measure the conductivity of medication 20. In some embodiment, the electrodes 38 may protrude out from the surface of plunger head 22 into barrel 12 where the electrodes 38 may contact medication 20. With the density, conductivity, and viscosity of medication 20 determined, microcontroller 26 may have a sufficient number of properties to profile medication 20. In some embodiments, the profiling may be configured to differentiate medication 20 in order to determine if it from a prescribed class of medication. In some embodiments, the profiling may be configured to verify that medication 20 is the same as the medication that is prescribed for the patient. In some embodiments, the profiling may be configured to identify the medication 20.

According to an exemplary embodiment, plunger head 22 as described herein may be combined with a syringe that has been modified to include a piezo linear motor. The piezo linear motor may be incorporated into the wall of the barrel of the syringe and a piezo element may be incorporated into plunger head 22. The piezo linear motor may be configured to drive or "walk" the plunger head 22 down the barrel of the syringe by driving the piezo element, thereby forcing the medication from the syringe. This embodiment may enable the piezo linear motor to control medication dispensing while plunger head 22 may simultaneously track the amount of medication being dispensed. In some embodiments, plunger head 22 may control the piezo linear motor or plunger head 22 can communication with a remote device that can control the piezo linear motor such that it dispenses a set amount of medication.

Figure 4:
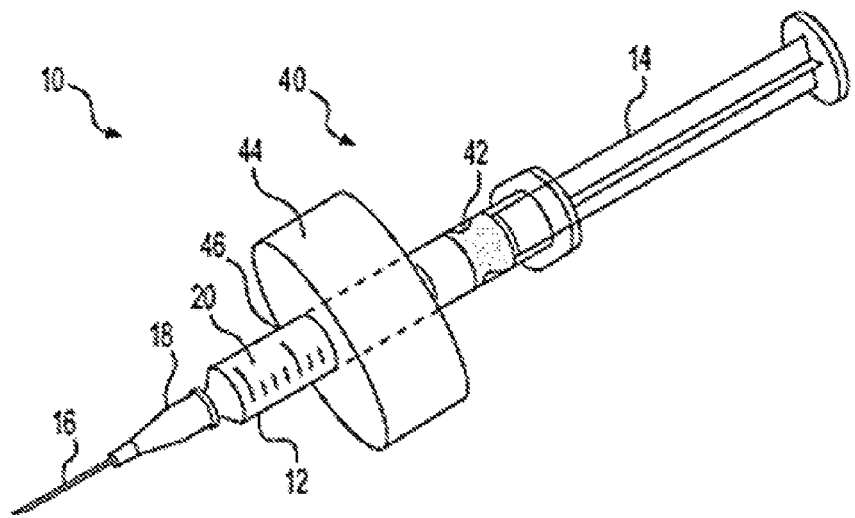
FIG. 4 is a perspective view of a syringe, which includes a plunger head and a cuff according to an exemplary embodiment.

FIG. 4 shows a smart syringe system 40, according to an exemplary embodiment. System 40 may be designed for use with a standard disposable syringe 10. Similar to plunger head 22, smart syringe system 40 may be configured to measure and register the quantity of medication 20 administered and the date and time of administration. Smart syringe system 40 may include a smart or intelligent plunger head 42, similar to plunger head 22, and a cuff 44. In some embodiments, plunger head 42 may be designed to be disposable after a single use while cuff 44 is reusable. Embodiments of plunger head 42 designed to be disposable after a single use may houses only the minimum number of components to carry out its function while any optional or ancillary components may be housed in cuff 44 to minimize manufacturing cost of plunger head 42. The manufacturing cost of plunger head 42 may also be minimized by using lower cost components (e.g., transducers, antennas, and microcontrollers) and materials (e.g., rubbers, polymers, plastics) that are less robust and durable, and instead may be designed for shorter operational life spans.

Plunger head 42 may be designed to be supplied with or installed into a disposable syringe 10 and after administering a dose of medication 20, syringe 10 along with plunger head 42 may be disposed of or recycled. In contrast, cuff 44 may be designed to be reused numerous times. For example, a disposable syringe 10 may be inserted through cuff 44 and after medication 20 is administered; cuff 44 may be removed from the used syringe 10 and be saved for later use.

In some embodiments, both plunger head 42 and cuff 44 may be reusable. For example, after medication 20 is administered by syringe 10, both plunger head 42 and cuff 44 may be removed and saved for later use.

Plunger head 42 and cuff 44 can come in different sizes so they may be used with any size syringe. For example, plunger head 42 may be sized to fit within the barrel 12 of any size syringe 10 while cuff 44 may be configured to have a passage 46 configured to receive any size barrel 12 of syringe 10.

Plunger head 42 and cuff 44 (i.e., the smart syringe system 40) in combination may be configured to have some or all of the same components (e.g., a transducer 24, a microcontroller 26, a power source 28, an antenna 30, crystal oscillator 32, force sensor 34, and a temperature sensor 36) as plunger head 22 and perform at least all the same operations as plunger head 22. Some of the components may be housed in plunger head 42 while some of the components may be housed in cuff 44. To reduce the manufacturing cost of plunger head 42, as described above, plunger head 42 may be designed to house the minimum number of components to carry out its functions. For example, system 40 may be configured such that all the components that can be housed in cuff 44 are, rather than plunger head 42. In some embodiments, such components may include a form of memory for data storage.

According to an exemplary embodiment, plunger head 42 may include the transducer 24, antenna 30, and a microcontroller 26 while cuff 44 may also include a separate microcontroller, a power source, and a separate antenna. To reduce complexity, plunger head 42 may be passive (e.g., battery-free) and configured to be controlled and powered by cuff 44 via wireless energy transmission. Cuff 44 may also be configured to communicate with a remote device (e.g., a smart phone) thereby enabling the volume of medication and the time and date of administering to be uploaded to another device or the cloud.

In some embodiments, cuff 44 may include a display. Cuff 44 may be configured to display any alerts (e.g., high temperature or improper medication) to the user. Cuff 44 may also display the volume, date, and time after medication has been dispensed. The display may also be configured to allow user input (e.g., touch screen). For example, the user may program in the date, the time, the type of medication or other information.

Figure 5:
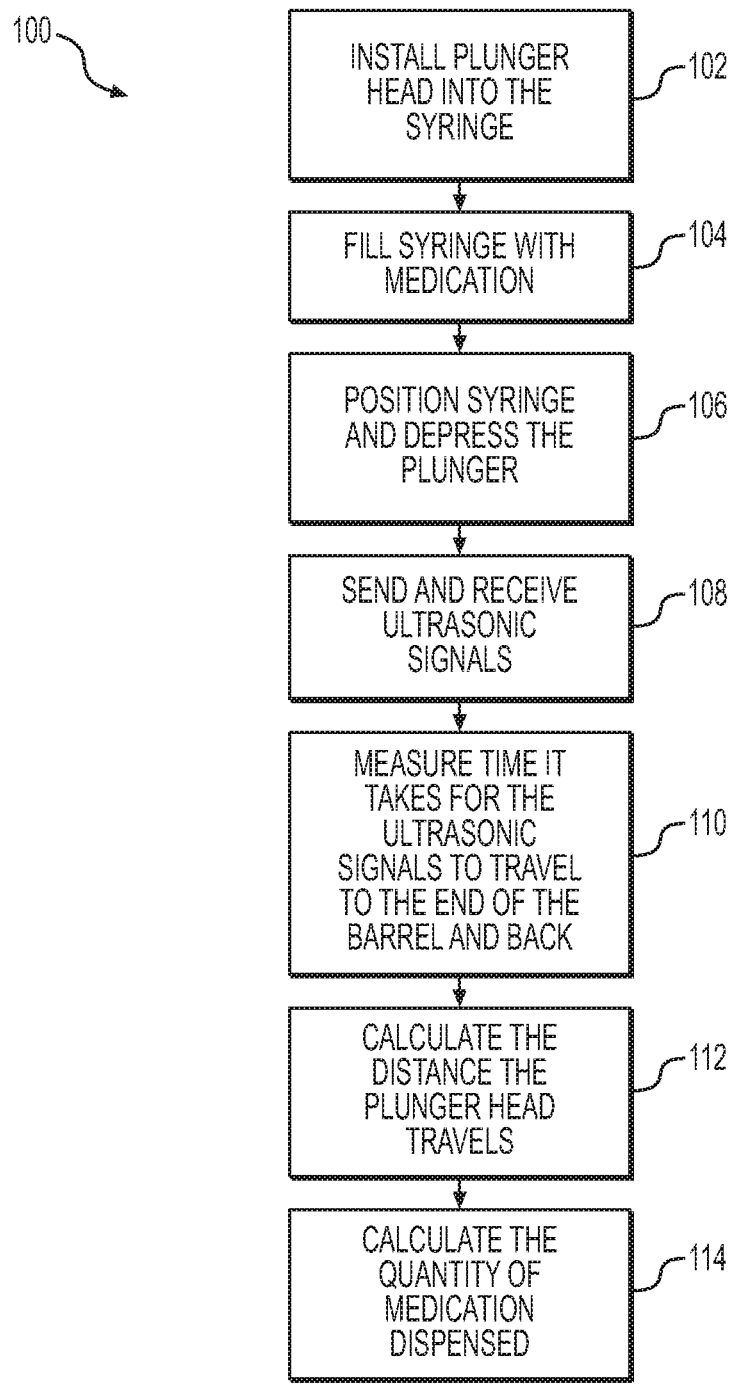
FIG. 5 is a flow chart illustrating a method of tracking administering of medication by syringe, according to an exemplary embodiment.

Plunger head 22 and system 40 described herein may be utilized for a variety of methods for tracking administering of a medication to a patient delivered by syringe. Various methods of utilizing plunger head 22 and system 40 will now be explained with reference to FIG. 5. In some embodiments, the methods as described herein may be performed by a caregiver (e.g., a doctor or nurse) in a hospital or other inpatient setting. In some embodiments, the methods as described herein may be performed by a caregiver (e.g., a doctor, nurse, or parent) at home or outside a hospital. In some embodiments, the methods as described herein may be performed by the patient. It is contemplated that the methods described herein may be performed in other settings by other individuals.

Plunger head 22 may be utilized for a method 100 of tracking administering of a medication to a patient delivered by a syringe, according to an exemplary embodiment. In some embodiments, at step 102, method 100 may begin by installing plunger head 22 into the barrel 12 of the syringe 10 (e.g., a disposable syringe). In some embodiments, the syringe 10 may be supplied with plunger head 22 already installed.

Next, at step 104, the barrel 12 of the syringe may be filled with the medication 20. The barrel 12 may be completely filled or only partially with medication 20. In some embodiments, the syringe 10 may be supplied prefilled with medication 20. In some embodiments, plunger head 22 may be configured to "wake up" in response to a force applied during the filling, which may be detected by force sensor 34.

Once filled, at step 106, the syringe may then be positioned for administration. For example, the needle may be inserted into the skin of the patient or into a drug delivery port connected to the patient. Once in position, the plunger 14 of the syringe 10 may be depressed, which forces plunger head 22 down the barrel 12 and forces the medication 20 out the needle 16.

In some embodiments, the initial position of plunger head 22 (e.g., the distance between plunger head 22 and end 27) may be known by plunger head 22. For example, syringe 10 may be full and plunger head 22 may know the distance between plunger head 22 and end 27 when filled. In some embodiments, if syringe 10 is used multiple times to deliver a medication 20, the previous position of plunger head 22 may be known from the last measurement stored. In some embodiments, the initial position of plunger head 22 may be measured using plunger head 22 prior to any medication 20 being delivered, as described below.

Prior to and while plunger 14 is being depressed, plunger head 22 may send and receive ultrasonic signals 25 via transducer 24, at step 108. Plunger head 22 may send and receive ultrasonic signals 25 the duration of the time the plunger is being depressed. Plunger head 22 may measure a time it takes for each of the ultrasonic signals to travel through the medication to an end of the barrel and return to the transducer, at step 110. In some embodiments, at least a portion of the ultrasonic signals 25 may be sent and received before any medication 20 is dispensed enabling the initial position of plunger head 22 and initial volume of medication 20 to be calculated.

As described herein, at step 112, plunger head 22 may calculate the distance the plunger head 22 travels over the course of dispensing medication 20. At step 114, the quantity of medication 20 dispensed may be calculated based on the calculated distance the plunger head 22 traveled.

For some embodiments of method 100, the calculation of the quantity of medication dispensed may be performed by a remote device (e.g., a smart phone). In some embodiments, method 100 may also include transmitting the quantity of the medication dispensed and the time and date the quantity was dispensed to a remote device. In some embodiments, method 100 may also include uploading the quantity of the medication dispensed and the time and date the quantity was dispensed to the cloud. In some embodiments, method 100 may also include sending the quantity of the medication dispensed and the time and date the quantity was dispensed to a caregiver.

Although method 100 is described with reference to plunger head 22, it may also be performed by system 40, as described herein.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described embodiments of plunger head 22, 42 and cuff 44 may be adapted for used with a variety of other medication injection devices, including for example, auto-injectors, auto-syringes, injector pens (e.g., insulin pens), or other drug or medication injection devices.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Computer programs, program modules, and code based on the written description of this specification, such as those used by the microcontrollers, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

Other embodiments will be apparent from consideration of the specification and practice of the embodiments disclosed herein. It is intended that the specification and examples be considered as example only, with a true scope and spirit of the disclosed embodiments being indicated by the following claims.

The invention claimed is:

1. A plunger head for a syringe, comprising:
   an ultrasonic transducer disposed within the plunger head for sending and receiving ultrasonic signals from the plunger head;
   an antenna;
   a microcontroller that interfaces with the ultrasonic transducer and the antenna; and
   a power source that powers the microcontroller and the ultrasonic transducer, wherein the ultrasonic transducer, the antenna, the microcontroller, and the power source are at least partially encapsulated in an elastomer housing that fits within a barrel of the syringe, wherein the ultrasonic transducer is positioned within the plunger head to propagate the ultrasonic signals from the plunger head along a length of the barrel extending towards a dispensing end of the barrel when the plunger head is inserted in the syringe; and
   wherein the microcontroller includes instructions to calculate data representative of a quantity of medication dispensed from the barrel and transmit the data to a remote device via the antenna, wherein the instructions, when executed by the microcontroller, cause the microcontroller to calculate the quantity of medication dispensed by:
      measuring a time for the ultrasonic signals to travel from the ultrasonic transducer to the dispensing end of the barrel and return to the ultrasonic transducer.

2. The plunger head of claim 1, wherein the microcontroller registers a date and time the medication is dispensed and transmits the date and time to the remote device along with the quantity of medication dispensed.

3. The plunger head of claim 1, further comprising a temperature sensor that measures a temperature of the medication, wherein the plunger head compensates for changes in the temperature of the medication when calculating the data representative of the quantity of medication dispensed.

4. The plunger head of claim 1, further comprising electrodes that measure a conductivity of the medication, wherein the plunger head using the ultrasonic signals measures a density, and a viscosity of the medication, and based on the conductivity, the density, and the viscosity, the plunger head profiles the medication.

5. The plunger head of claim 1, further comprising a crystal oscillator that keeps a time and date, wherein the crystal oscillator is a 10 MHZ crystal oscillator, which provides sufficient time accuracy to enable a position of the plunger head to be measured to within 150 microns.

6. The plunger head of claim 1, wherein the power source is rechargeable via an inductive charging system.

7. The plunger head of claim 1, wherein the plunger head detects air bubbles in the medication within the barrel by receiving echoes within the ultrasonic signals with the ultrasonic transducer.

8. The plunger head of claim 1, wherein the microcontroller is configured to store the data representative of the quantity of medication dispensed from the barrel until the remote device initiates transmission of the data to the remote device.

9. The plunger head of claim 1, wherein the instructions, when executed by the microcontroller, cause the microcontroller to calculate the quantity of medication dispensed by further:
   calculating a position of the plunger head within the syringe based on the measuring; and
   calculating the quantity of medication dispensed based on changes in the position.

10. The plunger head of claim 1, further comprising a force sensor, wherein the plunger head determines when dispensing of the medication is initiated based on a force detected by the force sensor.

11. The plunger head of claim 10, wherein the plunger head operates in a low-power sleep mode until dispensing of the medication is initiated and then the ultrasonic transducer begins sending and receiving the ultrasonic signals.

12. A plunger head for a medication injection device, comprising:
   an ultrasonic transducer disposed within the plunger head for sending and receiving ultrasonic signals from the plunger head;
   an antenna;
   a microcontroller that interfaces with the ultrasonic transducer and the antenna; and
   a power source that powers the microcontroller and the ultrasonic transducer, wherein the ultrasonic transducer, the antenna, the microcontroller, and the power source are at least partially encapsulated in an elastomer housing that fits within a barrel of the medication injection device, wherein the ultrasonic transducer is positioned within the plunger head to propagate the ultrasonic signals from the plunger head along a length of the barrel extending towards a dispensing end of the barrel when the plunger head is inserted in the medication injection device; and
   wherein the microcontroller includes instructions to calculate data representative of a quantity of medication dispensed from the barrel and transmit the data to a remote device via the antenna, wherein the instructions, when executed by the microcontroller, cause the microcontroller to calculate the quantity of medication dispensed by:
      measuring a time for the ultrasonic signals to travel from the ultrasonic transducer to the dispensing end of the barrel and return to the ultrasonic transducer.

* * * * *